(12) United States Patent
Tsai et al.

(10) Patent No.: US 9,086,341 B2
(45) Date of Patent: Jul. 21, 2015

(54) MULTI-FILTER PM 10-PM 2.5 SAMPLER

(75) Inventors: Chuen-Jinn Tsai, Hsinchu County (TW); Chun-Nan Liu, Taipei (TW)

(73) Assignee: NATIONAL CHIAO TUNG UNIVERSITY, Hsinchu (TW)

(*) Notice: Subject to any disclaimer, the term of this patent is extended or adjusted under 35 U.S.C. 154(b) by 461 days.

(21) Appl. No.: 13/419,532

(22) Filed: Mar. 14, 2012

(65) Prior Publication Data
US 2013/0036837 A1   Feb. 14, 2013

(30) Foreign Application Priority Data

Aug. 10, 2011 (TW) .............................. 100128556 A

(51) Int. Cl.
*G01N 1/22* (2006.01)
(52) U.S. Cl.
CPC ...... *G01N 1/2208* (2013.01); *G01N 2001/2223* (2013.01)
(58) Field of Classification Search
CPC ... B01D 46/10; G01N 1/2202; G01N 1/2205; G01N 1/2208; G01N 1/2273; G01N 1/24; G01N 2001/2223; G01N 2015/0261
USPC .................... 73/863, 863.02, 863.03, 863.21, 73/863.22, 863.23, 863.31, 863.41, 863.61
See application file for complete search history.

(56) References Cited

U.S. PATENT DOCUMENTS

| | | | |
|---|---|---|---|
| 3,501,899 A * | 3/1970 | Allen .............................. 96/397 |
| 4,827,779 A * | 5/1989 | Marple et al. .............. 73/863.22 |
| 5,016,482 A * | 5/1991 | Clingman et al. ......... 73/863.61 |
| 6,205,842 B1 * | 3/2001 | Patashnick et al. .......... 73/28.01 |
| 6,240,768 B1 * | 6/2001 | Lemonnier .................. 73/28.05 |
| 6,786,105 B1 * | 9/2004 | Sioutas ....................... 73/863.22 |
| 7,073,402 B2 * | 7/2006 | Trakumas et al. ......... 73/863.22 |
| 7,261,008 B2 * | 8/2007 | Saaski et al. ............... 73/863.22 |
| 7,370,543 B2 * | 5/2008 | Chen et al. ................. 73/863.21 |
| 7,597,015 B2 * | 10/2009 | Harley ......................... 73/865.5 |
| 8,733,185 B2 * | 5/2014 | Solomon ..................... 73/863.22 |
| 2001/0045000 A1 * | 11/2001 | Gundel et al. ................... 29/458 |
| 2005/0247868 A1 * | 11/2005 | Call et al. ....................... 250/282 |
| 2007/0044577 A1 * | 3/2007 | Trakumas et al. ......... 73/863.22 |
| 2007/0269349 A1 * | 11/2007 | Shih et al. ..................... 422/101 |
| 2010/0089183 A1 * | 4/2010 | Solomon ..................... 73/863.22 |

OTHER PUBLICATIONS

Yang Weixin, "Development of a Multi-Channel PM10-PM2.5 Sampler", added to the National Digital Library of Theses and Disertations in Taiwan on Sep. 30, 2009, <http://handle.ncl.edu.tw/11296/ndltd/88504661765931569834>.*

(Continued)

*Primary Examiner* — David A Rogers
(74) *Attorney, Agent, or Firm* — Bacon & Thomas, PLLC

(57) ABSTRACT

A multi-filter PM 10-PM 2.5 sampler which enable the simultaneous collection of four PM 10 and four PM 2.5 samples is disclosed. The sampler is provided with a PM 10 impactor to remove coarse particles and operates at 33.4 L/min. After the PM 10 impactor, the aerosol flow is divided by half by a branch pipe. Half of the flow is directed into four PM 10 cassettes, while the other half is directed into four PM 2.5 cassettes after the aerosols are further classified by a PM 2.5 impactor. To ensure the aerosol flow uniformly passes through each of the four PM 10 or four PM 2.5 cassettes, an orifice plate is assembled behind each of the filter cassettes to increase the pressure drop, such that the flow rates of eight sampling lines are nearly equal.

5 Claims, 3 Drawing Sheets

(56) References Cited

OTHER PUBLICATIONS

Dennis R. Fitz & Judith Zwicker, Design and Testing of the SCAQS Sampler for the SCAQS Study, 1987, Report # AV-FR-86/649, Aero Vlronment, Monrovia, C.A.

Watson, J. G. & Chow, J. C., Ambient Air Sampling. In: Aerosol Measurement: Principles, Techniques, and Applications, 2nd edn., P.A. Brown and K. Willeke, Eds., Wiley-Interscience, Hoboken, NJ, 2001: 821-824.

Chun-Nan Liu, Sheng-Chieh Chen & Chuen-Jinn Tsai (2011); A Novel Muilifilter PM10-PM2.5 Sampler (MFPPS), Aerosol Science and Technology, 45:12, 1480-1487.

* cited by examiner

US 9,086,341 B2

MULTI-FILTER PM 10-PM 2.5 SAMPLER

BACKGROUND OF THE INVENTION

1. Field of the Invention

The present invention relates generally to an aerosol sampler, and more particularly, to a multi-filter sampler for collecting PM 10 and PM 2.5 samples simultaneously.

2. Description of the Related Art

U.S. Patent Application No. 2010/0089183 disclosed a multi-filter sampler, which classifies particles by means of an impaction separator. Coarse particles with the aerodynamic diameter of 2.5-10 μm are led to pass through a first separation assembly and are collected by a 102 mm filter paper and three 47 mm filter papers, while fine particles having an aerodynamic diameter smaller than 2.5 μm pass through a second separation assembly and are collected by an 8×10 inch filter and four 47 mm filters. The user is consequently able to obtain the ambient air quality information by analyzing the filters. However, the filter cassettes have different flow rates from one another, so it is inconvenient to calibrate or operate the sampler, which results in inaccurate sampling.

SUMMARY OF THE INVENTION

The primary objective of the present invention is to provide a multi-filter PM 10-PM 2.5 sampler, which is capable of collecting PM 10 and PM 2.5 samples simultaneously and has a better accuracy.

The foregoing objective of the present invention is attained by the multi-filter PM 10-PM 2.5 sampler composed of a PM 10 impactor, a branch pipe, a PM 10 flow splitter, a plurality of PM 10 filter devices, a PM 2.5 impactor, a PM 2.5 flow splitter, a plurality of PM 2.5 filter devices, a conflux assembly, a plurality of flow uniformization devices, and an air pump. The branch pipe includes a top end, a left end, and a right end. The PM 10 impactor is connected with the top end of the branch pipe. The PM 10 flow splitter includes an inlet and a plurality of outlets. The inlet of the PM 10 flow splitter is connected with the left end of the branch pipe and the outlets are connected with the PM 10 filter devices separately. The PM 2.5 impactor is connected with the right end of the branch pipe. The PM 2.5 flow splitter includes an inlet and a plurality of outlets. The inlet of the PM 2.5 flow splitter is connected with the PM 2.5 impactor. The PM 2.5 filter devices are connected with the outlets of the PM 2.5 flow splitter. The flow uniformization devices are connected between the PM 10 filter devices and the conflux assembly and between the PM 2.5 filter devices and the conflux assembly, which make the flow rates even by reducing the pressure drop differences among the filter devices of the PM 10 and PM 10 filter devices. The air pump is connected with the conflux assembly.

In one of the preferred embodiments of the present invention, each of the PM 10 impactor and the PM 2.5 impactor includes an external housing, a nozzle, and an impact plate. The external housing has a chamber and an exit. The nozzle is mounted to the external housing and has an acceleration passage communicating with the chamber. The impact plate is mounted inside the chamber and located on an imaginary axis extension line of the acceleration passage. The multi-filter PM 10-PM 2.5 sampler further includes a protective mesh mounted to a top end of the PM 10 impactor. The multi-paper PM 10-PM 2.5 sampler further includes a plurality of flow uniformization devices mounted between the PM 10 filter devices and the conflux assembly or between the PM 2.5 filter devices and the conflux assembly. The uniformization device includes an upper member, an orifice plate and an lower member. The upper member has an axial hole including a smaller-diameter portion, a threaded portion, and a larger-diameter portion located between the smaller-diameter portion and the threaded portion for receiving the orifice plate. The lower member has a threaded portion and an axial hole, the axial hole being located inside the threaded portion, the threaded portion engaging with the threaded portion of the axial hole of the upper member, the axial hole of the lower member communicating with the smaller-diameter portion of the axial hole via a through hole of the orifice plate. The conflux assembly includes a PM 10 conflux device, a PM 2.5 conflux device, and a terminal conflux device. The PM 10 conflux device has a plurality of entrances and an exit. Each of the entrances of the PM 10 conflux device is connected with one of the PM 10 filter devices. The PM 2.5 conflux device has a plurality of entrances and an exit. Each of the entrances of the PM 2.5 conflux device is connected with one of the PM 2.5 filter devices. The terminal conflux device is connected among the exit of the PM 10 conflux device, the exit of the PM 2.5 conflux device, and the air pump. The multi-filter PM 10-PM 2.5 sampler further includes two mass flow controllers, a pressure sensor, a temperature sensor, and a control PC. The mass flow controller, the pressure sensor, the temperature sensor, and the air pump are electrically connected with the control PC.

DETAILED DESCRIPTION OF PREFERRED EMBODIMENTS

Figure 1:
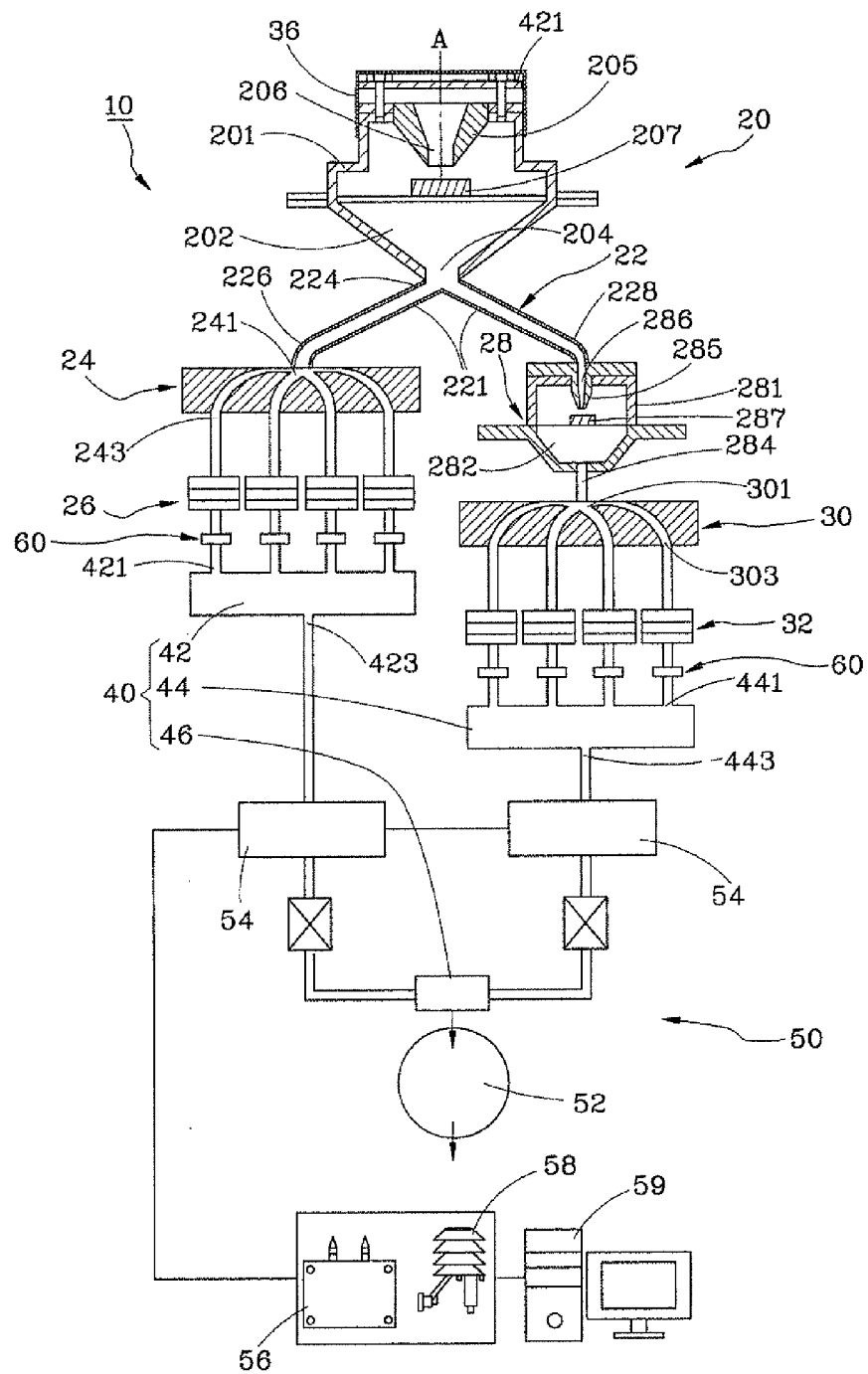
FIG. 1 is a schematic view of a preferred embodiment of the present invention.

Referring to FIG. 1, a multi-filter PM 10-PM 2.5 sampler 10 constructed according to a preferred embodiment of the present invention is composed of a PM 10 impactor 20, a branch pipe 22, a PM 10 flow splitter 24, four PM 10 filter devices 26, a PM 2.5 impactor 28, a PM 2.5 flow splitter 30, four PM 2.5 filter devices 32, a protective mesh 36, a conflux assembly 40, a flow control system 50, and a plurality of flow uniformization devices 60. The detailed descriptions and operations of these elements as well as their interrelations are recited in the respective paragraphs as follows.

The PM 10 impactor 20 includes an external housing 201, a nozzle 205, and an impact plate 207. The external housing 201 has a chamber 202 and an exit 204. The nozzle 205 is mounted to the external housing 201 and has an acceleration passage 206 in communication with the chamber 202. The impact plate 207 is mounted inside the chamber 202 and located on an imaginary axis extension line A of the acceleration passage 206.

The branch pipe 22 is composed of two tubular members 221 and includes a top end 224, a left end 226, and a right end 228. The top end 224 is connected with the exit 204 of the PM 10 impactor 20 for dividing the airflow passing through the PM 10 impactor 20 into two parts.

Figure 2:
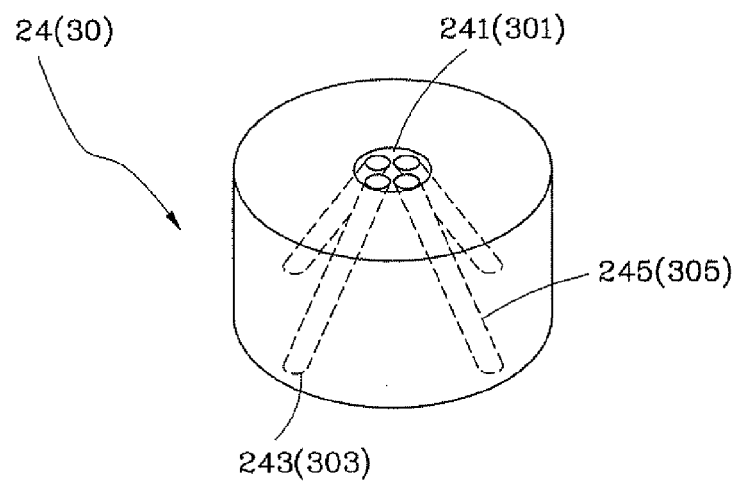
FIG. 2 is a perspective view of a part of the preferred embodiment of the present invention, illustrating a flow splitter.

The PM 10 flow splitter 24, as shown in FIG. 2, includes an inlet 241, four outlets 243, and four channels 245. The channels 245 are arranged equiangularly and communicate with the inlet 241 and the outlet 243 for dividing the airflow into four parts.

Figure 3:
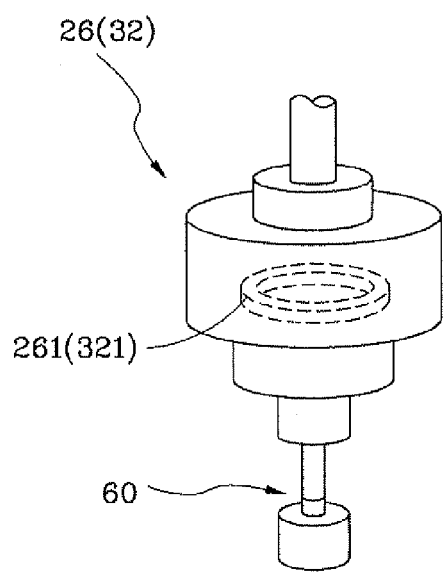
FIG. 3 is a perspective view of parts of the preferred embodiment of the present invention, illustrating a filter device and a flow uniformization device.

Each of the PM 10 filter devices 26, as shown in FIG. 3, is connected with one of the outlets 243 of the PM 10 flow splitters 24 and internally includes a filter cassette 261, in which a 37 mm filter paper is provided, for collecting PM 10 particle samples.

The PM 2.5 impactor 28 likewise includes an external housing 281, a nozzle 285, and impact plate 287. The external housing 281 has a chamber 282 and an exit 284. The nozzle 285 is mounted to the external housing 281 and has an acceleration passage 286 communicating with the chamber 282. The impact plate 287 is mounted inside the chamber 282 and located on an axis extension line of the acceleration passage 286. The PM 2.5 impactor 28 and the PM 10 impactor 20 are structurally similar to each other but different in size and cutoff aerodynamic diameter; the cutoff aerodynamic diameter of the former is 2.5 μm and the latter 10 μm.

The PM 2.5 flow splitter 30 (FIG. 2) is similar to the PM 10 flow splitter 24 in structure and size, likewise having an inlet 301, four outlets 303, and four channels 305 arranged equiangularly and communicating with the inlet 301 and the outlets 303.

Each of the PM 2.5 filter devices 32 (FIG. 3) is connected with one of the outlets 303 of the PM 2.5 flow splitter 30 and internally includes a filter cassette 321, in which a 37 mm filter paper is provided, for collecting PM 2.5 particle samples.

The protective mesh 36 is made of metal and mounted to a top end of the PM 2.5 impactor 20 for preventing any insect or other foreign matter from entering the PM 10 impactor 20.

The conflux assembly 40 includes a PM 10 conflux device 42, a PM 2.5 conflux device 44, and a terminal conflux device 46. The PM 10 conflux device 42 includes a plurality of entrances 421 and an exit 423. Each of the entrances 421 is connected with one of the PM 10 filter devices 26. The PM 2.5 conflux device 44 likewise includes a plurality of entrances 441 and an exit 443. Each of the entrances 441 is connected with one of the PM 2.5 filter devices 32. The terminal conflux device 46 is connected among the exit 423 of the PM 10 conflux device 42 and the exit 443 of the PM 2.5 conflux device 44.

The flow control system 50 includes an air pump 52, two mass flow controllers 54, a pressure sensor 56, a temperature sensor 58, and a control PC 59. The air pump 52 is connected with the terminal conflux device 46 for providing pumping power for the sampler 10. One of the mass flow meters 54 is connected between the PM 10 conflux device 42 and the terminal conflux device 46 and the other is connected between the PM 2.5 conflux device 44 and the terminal conflux device 46. The control PC 59 is electrically connected with the air pump 52, the mass flow controllers 54, the pressure sensor 56, and the temperature sensor 58. The standard flow rate of mass flow controllers 54 is adjusted automatically based on the ambient temperature and pressure obtained by the pressure sensor 56, and the temperature sensor 58.

Figure 4:
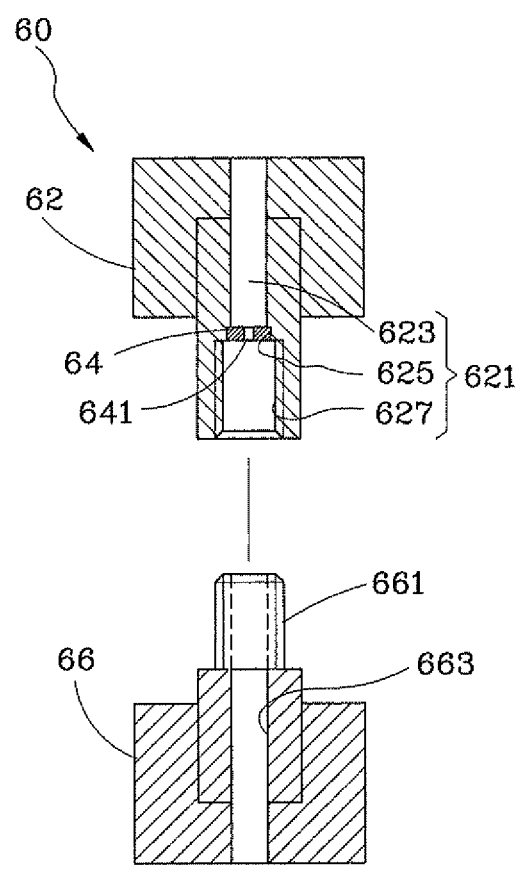
FIG. 4 is a sectional exploded view of the preferred embodiment of the present invention, illustrating the flow uniformization device.

The flow uniformization devices 60 (FIGS. 3-4) are connected between the PM 10 filter devices 26 and the PM 10 conflux device 42 or between the PM 2.5 filter device 32 and the PM 2.5 conflux device 44. Each of the flow uniformization devices 60 includes an upper member 62, an orifice plate 64, and a lower member 66. The upper member 62 is connected with the filter device 26 or 32 and has an axial hole 621 with a smaller-diameter portion 623, a larger-diameter portion 625, and a threaded part 627. The larger-diameter portion 625 is located between the smaller-diameter portion 623 and the threaded part 627 for receiving the orifice plate 64. The orifice plate 64 has a small through hole 641. The lower member 66 has a threaded portion 661 and an axial hole 663. The threaded portion 661 engages with the threaded part 627 of the axial hole 621 of the upper member 62. The axial hole 663 of the lower member 66 communicates with the smaller-diameter portion 623 of the upper member 62 via the through hole 641 of the orifice plate 64.

While the air pump 52 is operated, aerosols are guided into the sampler 10 at 33.4 L/min via an annular slot inlet 21. After the inlet 21, the PM 10 impactor 20 is used to remove particles greater than 10 μm in aerodynamic diameter. Aerosol flow is then divided into two stream of equal flow rate of 16.7 L/min by the smooth branch pipe 22, one stream is led to four PM 10 filter devices 26 behind the PM 10 flow splitter 24, and the other is introduced into the PM 2.5 impactor 28. After the PM 2.5 impactor 28, the aerosol stream is divided by the PM 2.5 splitter 30 into four PM 2.5 filter devices. The flow control system 50 is used to control the total actual sampling flow rate of both PM 10 and PM 2.5 at 16.7 L/min using the feedback signals of ambient temperature and pressure.

The PM 10 filter devices 26 and the PM 2.5 filter device 32 are able to collect four PM 10 filter samples and four PM 2.5 filter samples at the same time for further analysis, such as gravimetric analysis, organic carbon analysis, elemental carbon analysis, metallic element analysis, ionic analysis, etc., thus avoiding the inaccuracy resulting from cutting the filter paper and saving the cost caused by installing multiple samplers.

When filters of different types are used, the pressure drops of the filter devices 26 and 32 are not equal due to the differences in filter porosity and thickness, and therefore the flow rates of the filter devices 26 and 32 are different. The orifice plate 64 of the flow uniformization device 60 is provided to enhance the pressure drop of each sampling channel of the filter devices 26 and 32 to lower the relative difference of pressure drop resulting from different filters. Table 1 show that when the orifice plates 64 are not used the maximum relative difference in the pressure drop created by Teflon filters is 10.3%, which is large due to the differences in the filters. The flow rates between sampling lines are shown to be non-uniform with a maximum relative difference of 9.1%. However, after the orifice plates 64 with the diameter of 1.1 mm are assembled behind the filter cassettes 261 and 321, the pressure drop in each sampling line is increased by nearly the same amount of about 40 cm $H_2O$, which reduces the relative differences in the pressure drop to less than 1.9%. Since the pressure drop differences are reduced, the flow rate uniformity between four sampling channels is achieved with a relative difference of less than 1.7%. The flow rates of all of the filter devices 26 and 30 are nearly the same to enable the sampler 10 to be calibrated or operated more easily and to enhance the accuracy of collection.

TABLE 1

Comparison of difference of pressure drops and flow rates of filter channels before he orifice plate is installed.

| | No Orifice Plate Installed | | Orifice Plate Installed | |
| --- | --- | --- | --- | --- |
| Channel No. | ΔP (cm$H_2O$)* | $Q_a$ (L/min)** | ΔP (cm$H_2O$)* | $Q_a$ (L/min)** |
| 1 | 13.75 | 3.90 | 54.68 | 4.12 |
| 2 | 14.37 | 3.75 | 54.99 | 4.07 |

TABLE 1-continued

Comparison of difference of pressure drops and flow rates of filter
channels before he orifice plate is installed.

| | No Orifice Plate Installed | | Orifice Plate Installed | |
|---|---|---|---|---|
| Channel No. | ΔP (cmH$_2$O)* | Q$_a$ (L/min)** | ΔP (cmH$_2$O)* | Q$_a$ (L/min)** |
| 3 | 13.03 | 4.09 | 53.95 | 4.14 |
| 4 | 13.54 | 3.97 | 54.37 | 4.13 |
| Max Relative Difference | 10.3% | 9.1% | 1.9% | 1.7% |

Note:
*The standard flow rate of each filter channel is controlled at 4.17 L/min.
**The standard flow rate sum of each filter channel is controlled at 16.7 L/min.

Although the present invention has been described with respect to a specific preferred embodiment thereof, it is in no way limited to the specifics of the illustrated structures but changes and modifications may be made within the scope of the appended claims.

What is claimed is:

1. A multi-filter PM10-PM2.5 sampler comprising:
   a PM 10 impactor;
   a branch pipe having a to end, a left end, and a right end, the to end being connected with the PM 10 impactor;
   a PM 10 flow splitter having a plurality of outlets and an inlet connected with the left end of the branch pipe;
   a plurality of PM 10 filter devices connected with the outlets of the PM 10 flow splitter, each PM 10 filter device having a sampling channel;
   a PM 2.5 impactor connected with the right end of the branch pipe;
   a PM 2.5 flow splitter having a plurality of outlets and an inlet connected with the PM 2.5 impactor;
   a plurality of PM 2.5 filter devices connected with the outlets of the PM 2.5 flow splitter, each PM 2.5 filter device having a sampling channel, each sampling channel having a pressure drop;
   a conflux assembly;
   a plurality of flow uniformization devices connected between the PM 10 filter devices and the conflux assembly and between the PM 2.5 filter devices and the conflux assembly for enhancing the pressure drop of each sampling channel so as to lower a relative difference in the pressure drop of the sampling channels; and
   an air pump connected with the conflux assembly;
   wherein each of the flow uniformization devices has an orifice plate with a through hole;
   wherein each of the flow uniformization device further comprises an upper member and a lower member, the upper member having an axial hole, the axial hole having a smaller-diameter portion, a larger-diameter portion, and a threaded part, the larger-diameter portion being located between the smaller-diameter portion and the threaded part for receiving the orifice plate, the lower member having a threaded portion and an axial hole located inside the threaded portion, the threaded portion engaging with the threaded part of the axial hole of the upper member, the axial hole of the lower member communicating with the smaller-diameter portion of the upper member via the through hole of the orifice plate.

2. The multi-filter PM10-PM2.5 sampler as defined in claim 1, wherein each of the PM 10 impactor and the PM 2.5 impactor comprises an external housing, a nozzle, and an impact plate, the external housing having a chamber and an exit, the nozzle being mounted to the external housing and having an acceleration passage communicating with the chamber, the impact plate being mounted inside the chamber and located on an imaginary extension line of the acceleration passage.

3. The multi-filter PM10-PM2.5 sampler as defined in claim 1 further comprising a protective mesh mounted to the top end of the PM 10 impactor.

4. The multi-filter PM10-PM2.5 sampler as defined in claim 1, wherein the conflux assembly comprises a PM 10 conflux device, a PM 2.5 conflux device, and a terminal conflux device, the PM 10 conflux device having a plurality of entrances and an exit, each of the entrances of the PM 10 conflux device being connected with one of the PM 10 filter device, the PM 2.5 conflux device having a plurality of entrances and an exit, each of the entrances of the PM 2.5 conflux device being connected with one of the PM 2.5 filter device, the terminal conflux device being connected among the exit of the PM 10 conflux device, the exit of the PM 2.5 conflux device, and the air pump.

5. The multi-filter PM10-PM2.5 sampler as defined in claim 1 further comprising two flow controllers, a pressure sensor, a temperature sensor, and a control PC, wherein the two flow controllers, the pressure sensor, the temperature sensor, and the air pump are electrically connected with the control PC.

* * * * *